United States Patent [19]

Fruehwirth

[11] Patent Number: Plant 7,308

[45] Date of Patent: Aug. 28, 1990

[54] POINSETTIA PLANT 127

[75] Inventor: Franz Fruehwirth, Encinitas, Calif.

[73] Assignee: Paul Ecke Ranch, Inc., Encinitas, Calif.

[21] Appl. No.: 263,492

[22] Filed: Oct. 27, 1988

[51] Int. Cl.[5] ..... A01H 5/00

[52] U.S. Cl. ..... Plt./86

[58] Field of Search ..... Plt./86

[56] References Cited

U.S. PATENT DOCUMENTS 4,724,276 2/1988 Ecke, Jr. ..... 800/1

*Primary Examiner*—James R. Feyrer

*Attorney, Agent, or Firm*—Arnold, White & Durkee

[57] ABSTRACT

A new Poinsettia cultivar named '127', particularly distinguished by its stable and uniform bract coloration of light pink flecks on dark red bracts. The poinsettia described herein is a sport of the poinsettia cultivar described in U.S. Plant Pat. No. 2,923, is a more vigorous plant and branches more freely than the cultivar of U.S. Plant Pat. No. 3,889. The bract color is darker and the contrast between the colors is greater than that of U.S. Plant Pat. No. 4,860.

1 Drawing Sheet

BACKGROUND OF THE INVENTION

'127' is a stiff-stemmed, vigorous Poinsettia with attractive bicolored red and pink flower bracts. Red is the predominant color with pink flecks of various sizes and shapes randomly scattered over the bracts. The plant has self-branching traits which increases its value as a flowering branched plant.

This new poinsettia cultivar originated as a sport of the cultivar described in U.S. Plant Pat. No. 2,923 in a greenhouse in Encinitas, Calif. It was selected because of traits which distinguish it from other Poinsettia cultivars and seem to make it a desirable plant for commercial greenhouse production. It is a more vigorous plant and branches more freely than the cultivar described in the U.S. Plant Pat. No. 3,889. The bract color is darker and the contrast between the colors is greater than the Poinsettia described in U.S. Plant Pat. No. 4,860. Moreover, the bracts are more erect and do not droop like the cultivar of U.S. Plant Pat. No. 4,860, giving it a lively and fresh appearance. After selection, vegetatively reproduction of this plant by stem cuttings for test purposes in Encinitas, Calif., and clones of the plant were subjected to successive generations of vegetative propagation. The bract colors and the percentage of each color in the flower bracts remain stable from generation to generation.

DESCRIPTION OF THE PHOTOGRAPHS

The Poinsettia of the present invention, cultivar '127', is illustrated in the accompanying color photographs. The upper photo is a side view of a typical branched plant in full flower. The lower photo is a top view of a plant showing flower and bract formation.

DESCRIPTION OF THE PLANT

The following is a detailed description of this new poinsettia as observed in a greenhouse in Encinitas, Calif., during December, 1987. Recorded observations from flowering plants, grown as 3 unpinched plants per pot were observed. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Color sport of the cultivar of C-1 Red U.S. Plant Pat. No. 2,923, the sport being induced to be self-branching by the process described in U.S. Pat. No. 4,724,276.

Classification:

*Botanic.*—*Euphorbia pulcherrima* Willd.

*Common name.*—Poinsettia.

*Cultivar name.*—'127'.

Form: Shrub.

Height: Medium.

Growth habit: As a single stemmed plant, upright and vigorous. In full flower, the stem is terminated by a large inflorescence, with several smaller flowering side shoots lower on the stem. Observation of 3 plants in a pot with an overall height of 42 cm. and an overall width of 48 cm. were made. The bract diameter of individual flowers was 35 cm.

Branching: Branching can be enhanced by removal of the stem tip. Then, several flowering branches with equal vigor may develop on a single plant.

Growth rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of medium size, leaf blades typically being about 13–15 cm. long and about 7–9 cm. wide with leaf petioles about 5–7 cm long.

Leaf shape: Typical leaves are ovate with obtuse bases and acuminate tips. Leaf margins are mostly entire, some with slight lobing and minor indentations on each side of the leaf blade.

Color:

*Upper side.*—Darker than RHS 137A.

*Under side.*—Near RHS 138B.

Retention: The foliage retention is good even under low light intensities in the consumer's home.

Bracts: Generally there are 21–24 bicolored red and pink bracts of various sizes subtending the cyathia. The primary bracts have blades typically 12–14 cm. long and 8–9 cm. wide with petioles about 3 cm. long.

Shape: Bracts are mostly ovate with acute bases and acuminate tips. Primary bracts are mostly entire with some slight lobing.

Color:

*Upper side.*—Bicolored: Dark red bracts with pink flecks. Red background near RHS 53B. Pink flecks near RHS 51C.

*Under side.*—Bicolored: Red near RHS 53B. Pink near RHS 50D.

Cyathia: Generally, 15–18 cyathia (flowers) are present when the plant is in "full bloom". Each cyathium is about 7 mm long and about 5 mm wide, light green in color, and fringed with red at the distal end. Usually one or two bright yellow nectar cups with some overlying red pigment, protrudes from the side of the cyathium. The flower pedicel is also light green and about 3–4 mm in length. The anthers protruding from the cyathia are reddish.

What is claimed is:

1. A new and distinct Poinsettia cultivar, substantially as herein shown and described, distinguished by its stable and uniform bract coloration of light pink flecks on dark red bracts.

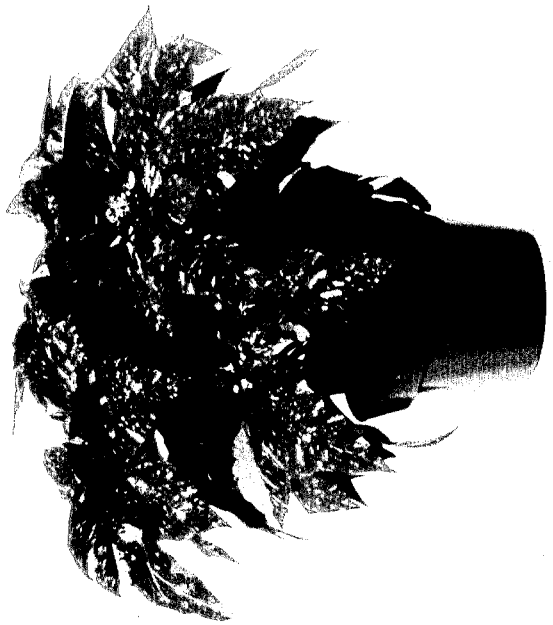
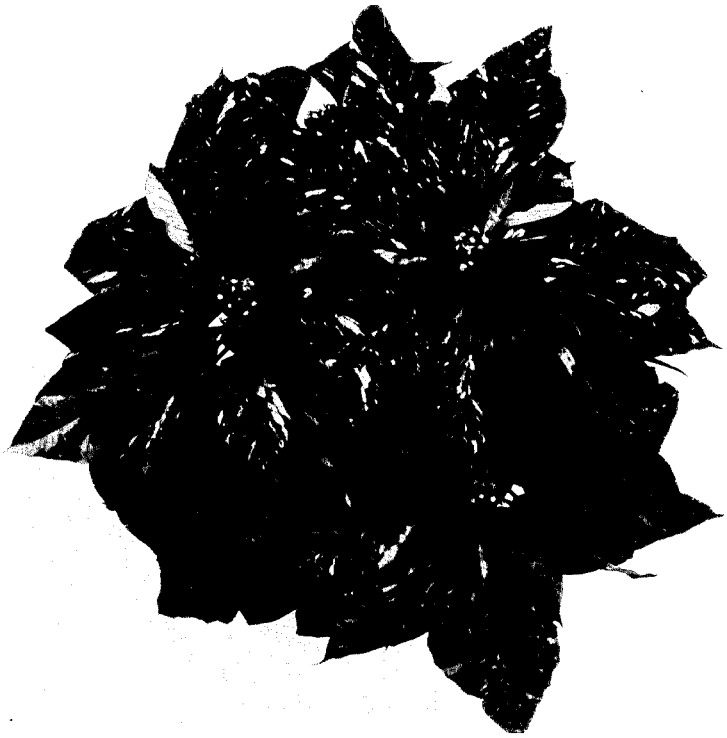

* * * * *